US009333259B2

(12) United States Patent
Almutairi et al.

(10) Patent No.: US 9,333,259 B2
(45) Date of Patent: May 10, 2016

(54) SELECTIVE FAT REMOVAL USING NIR LIGHT AND NANOPARTICLES

(71) Applicants: The Regents of the University of California, Oakland, CA (US); ELUX MEDICAL, INC., San Diego, CA (US)

(72) Inventors: Adah Almutairi, La Jolla, CA (US); Khalid Almutairi, La Jolla, CA (US)

(73) Assignees: The Regents of the University of California, Oakland, CA (US); eLux Medical, Inc., San Diego, CA (US)

( * ) Notice: Subject to any disclaimer, the term of this patent is extended or adjusted under 35 U.S.C. 154(b) by 35 days.

(21) Appl. No.: 14/464,629

(22) Filed: Aug. 20, 2014

(65) Prior Publication Data

US 2014/0358068 A1    Dec. 4, 2014

Related U.S. Application Data

(63) Continuation of application No. 14/379,488, filed as application No. PCT/US2013/040219 on May 8, 2013.

(60) Provisional application No. 61/644,328, filed on May 8, 2012.

(51) Int. Cl.
*A61N 5/06* (2006.01)
*A61K 41/00* (2006.01)
*A61B 18/04* (2006.01)
*A61B 18/20* (2006.01)
(Continued)

(52) U.S. Cl.
CPC ............. *A61K 41/0052* (2013.01); *A61B 18/04* (2013.01); *A61B 18/20* (2013.01); *A61K 33/24* (2013.01); *A61M 1/008* (2013.01); *A61N 5/062* (2013.01); *A61B 2018/00464* (2013.01); *A61M 2202/08* (2013.01); *A61N 2005/067* (2013.01); *A61N 2005/0626* (2013.01); *A61N 2005/0659* (2013.01)

(58) Field of Classification Search
CPC ..................... A61B 2018/00464; A61B 18/04; A61B 18/28; A61N 5/062; A61N 2005/0659; A61N 2005/067; A61K 41/0052; A61M 2202/08
USPC ............ 606/27, 33; 604/542, 20; 607/100, 89
See application file for complete search history.

(56) References Cited

U.S. PATENT DOCUMENTS 5,226,907 A    7/1993  Tankovich
5,425,728 A    6/1995  Tankovich
(Continued)

OTHER PUBLICATIONS

Samim, M., et al., "Synthesis and characterization of gold nanorods and their application for photothermal cell damage", International Journal of Nanomedicine, 2011:6 1825-1831.
(Continued)

*Primary Examiner* — Ronald Hupczey, Jr.
*Assistant Examiner* — Thomas Giuliani
(74) *Attorney, Agent, or Firm* — Eleanor Musick

(57) ABSTRACT

A system and method are provided for minimally-invasive selective removal of fat from a target area by injecting the area with a solution of photo-absorbing nanoparticles and irradiating the injected area with a beam of near infrared (NIR) light. The NIR emission wavelength excites the nanoparticles to melt fat within the target area so that the liquefied fat can be aspirated from the target area. The nanoparticles may be gold nanorods having aspect ratios selected to produce surface plasmon resonance when irradiated with NIR light around 800 nm.

28 Claims, 5 Drawing Sheets

(51) Int. Cl.
*A61M 1/00* (2006.01)
*A61K 33/24* (2006.01)
*A61B 18/00* (2006.01)
*A61N 5/067* (2006.01)

(56) References Cited

U.S. PATENT DOCUMENTS

| | | | |
|---|---|---|---|
| 5,817,089 | A | 10/1998 | Tankovich et al. |
| 6,063,074 | A | 5/2000 | Tankovich |
| 6,152,917 | A | 11/2000 | Tankovich |
| 6,165,440 | A | 12/2000 | Esenaliev |
| 6,302,863 | B1 | 10/2001 | Tankovich |
| 6,344,272 | B1 | 2/2002 | Oldenburg et al. |
| 6,530,944 | B2 | 3/2003 | West et al. |
| 6,605,080 | B1 | 8/2003 | Altshuler et al. |
| 6,685,927 | B2 | 2/2004 | Sumian et al. |
| 6,685,986 | B2 | 2/2004 | Oldenburg et al. |
| 7,276,088 | B2 | 10/2007 | Huang et al. |
| 7,371,457 | B2 | 5/2008 | Oldenburg et al. |
| 7,438,411 | B2 | 10/2008 | Payne et al. |
| 7,891,362 | B2 | 2/2011 | Domankevitz et al. |
| 8,057,418 | B2 | 11/2011 | Korbling |
| 8,357,146 | B2* | 1/2013 | Hennings et al. ............. 606/15 |
| 8,801,690 | B2 | 8/2014 | Peyman |
| 2004/0006328 | A1 | 1/2004 | Anderson |
| 2005/0175649 | A1 | 8/2005 | Disalvo et al. |
| 2005/0203495 | A1 | 9/2005 | Malak |
| 2007/0060989 | A1 | 3/2007 | Deem et al. |
| 2007/0208400 | A1* | 9/2007 | Nadkarni et al. ............. 607/100 |
| 2008/0241262 | A1* | 10/2008 | Lee et al. ............. 424/490 |
| 2008/0279946 | A1* | 11/2008 | Hainfeld ............. 424/489 |
| 2010/0057068 | A1* | 3/2010 | Lee ............. A61K 1/0052 606/27 |
| 2010/0294952 | A1* | 11/2010 | Mirkin et al. ............. 250/492.1 |
| 2011/0052672 | A1 | 3/2011 | Krishnan et al. |
| 2011/0059023 | A1 | 3/2011 | Tunnell et al. |
| 2011/0306956 | A1 | 12/2011 | Islam |
| 2012/0059307 | A1* | 3/2012 | Harris et al. ............. 604/20 |
| 2013/0225901 | A1 | 8/2013 | Krishnan et al. |
| 2014/0005593 | A1 | 1/2014 | Harris et al. |
| 2014/0012162 | A1 | 1/2014 | Harris et al. |
| 2014/0012163 | A1 | 1/2014 | Harris et al. |
| 2014/0012183 | A1 | 1/2014 | Harris et al. |

OTHER PUBLICATIONS

Zhan, Q., et al., Using 915 nm Laser Excited TM3+/Er3+/Ho3+-Doped NaYbF4 Upconversion Nanoparticles for in Vitro and Deeper in Vivo Bioimaging without Overheating Irradiation, ACS Nano, 2011, vol. 5, No. 5:3744-3757.

Zijlstra, P., "Photothermal properties of gold nanorods and their application to five-dimensional optical recording", Thesis, Centre for Micro-Photonics, Swinburne University of Technology (AU), Jun. 2009, pp. 8, 26, 61 and 101.

PCT/US2013/040219 International Search Report and Written Opinion, Jul. 24, 2013, 7 pages.

Bawa, R., "Nanoparticle-based Therapeutics in Humans: A Survey", Nanotechnology Law & Business, Summer 2008, pp. 135-155.

Yanina, I.Y., et al., "Effect of bacterial lectin on acceleration of fat cell lipolysis at in vitro diode laser treatment using encapsulated ICG", Saratov Fall Meeting 2011: Optical Technologies in Biophysics and Medicine XIII, 2012, Proc. of SPIE vol. 8337, pp. 83370E-1-83370E-7.

Tong, L., et al., "Gold nanorods as contrast agents for biological imaging: optical properties, surface conjugation, and photothermal effects", Photochem Photobiol. 2009; 85(1): 21. doi:10.1111/j.1751-1097.2008.00507.x.

Yanina, I.Y., et al., "Fat tissue histological study at indocyanine green-mediated photothermal/photodynamic treatment of skin in vivo", Journal of Biomedical Optics, May 2012, vol. 17(5), pp. 058002-1 to 058002-9.

* cited by examiner 1 min Irrad     3 min Irrad     3 min Irrad Backlit

SELECTIVE FAT REMOVAL USING NIR LIGHT AND NANOPARTICLES

RELATED APPLICATIONS

This application is continuation of application Ser. No. 14/379,488, filed Aug. 18, 2014, which is a 371 national stage filing of International Application No. PCT/US2013/040219, filed May 9, 2013, which claims the benefit of the priority of Application No. 61/644,328, filed May 8, 2012, which is incorporated herein by reference in its entirety.

FIELD OF THE INVENTION

The invention relates to a system, kit and method for reduction of fatty tissue in the body, and more particularly to removal of fatty tissue using near infrared laser light.

BACKGROUND OF THE INVENTION

Liposuction evolved from work in the late 1960s from surgeons in Europe using primitive curettage techniques which were largely ignored, as they achieved irregular results with significant morbidity and bleeding. Modern liposuction first burst on the scene in a presentation by the French surgeon, Dr Yves-Gerard Illouz, in 1982. The "Illouz Method" featured a technique of suction-assisted lipolysis after tumesing or infusing fluid into tissues using blunt cannulas and high-vacuum suction and demonstrated both reproducible good results and low morbidity. During the 1980s, many United States surgeons experimented with liposuction, developing variations, and achieving mixed results. Most commonly, liposuction is performed on the abdomen and thighs in women, and the abdomen and flanks in men. According to the American Society for Aesthetic Plastic Surgery, liposuction was the most common plastic surgery procedure performed in 2006 with 403,684 patients.

Traditional liposuction relies on two techniques. The first technique employs a sharp, relatively large diameter (3 mm-5 mm) cannula that is manually manipulated to mechanically break fat down and while applying suction to remove the separated fat. A variation of this vacuum assisted technique is a mechanically powered cannula that reduces the surgeon's fatigue during large surface area liposuction procedures.

The second technique utilizes ultrasonic waves via a vibrating cannula, this technique is mechanical in its nature and significantly reduces the surgeon's fatigue factor. This technique induces the same or worse mechanical trauma to the tissues. Both techniques require significant amounts of fluid, known as a "tumescent solution," to be injected into the body to emulsify the fat, facilitating the removal of large volumes of fat while reducing blood loss and delivering a local anesthetic (lidocaine) to provide post-operative pain relief. While generally safe, lidocaine can be toxic, leading to serious complications, and even death.

A problem with the probes used in existing liposuction procedures is the generation of significant amounts of heat at the distal tip of the probe, which can exceed the temperature required for melting the fatty tissue. This excess heat can result in burning of tissue, damaging muscles or blood vessels, and even penetrating membranes such as the skin or the peritoneum that covers most of the intra-abdominal organs.

Alternative methods have been disclosed which exploit laser energy to remove unwanted fat. U.S. Pat. Nos. 6,605,080 and 7,060,061 issued to Altshuler, et al. represent an alternative approach in which laser energy is externally applied to the skin to heat and melt fat tissues in epidermis and subcutaneous layers below. These patents disclose the use of near infrared radiation to heat-liquefy fat cells, after which the lipid pool is removed from the subcutaneous area by aspiration. Because of the considerable heat generation that results from the techniques, e.g., up to 70° C., at or in the fat tissue, a special cooling mechanism must be in place to prevent potential temporary skin damage or permanent scarring, with permanent scarring occurring primarily in the dermis. These methods present other limitations and potential adverse thermal effects on tissue above the lipid-rich tissue under treatment, including blistering, peeling, and depigmentation.

U.S. Pat. No. 8,430,919 of Bornstein discloses a lipolysis method in which the skin over the target site is optically irradiated with two different wavelengths of light, one in the near infrared (NIR) region, the other in the infrared range, to modulate biochemical processes of adipocytes in the target site. In order to achieve the desired degree of fat removal, the duration of the treatment must be fairly long, from one to two hours, during which the patient must remain virtually motionless. Unless a sedative or general anesthesia has been administered to calm the patient, physical and psychological discomfort can ensue.

NIR (700-950 nm) is preferable to other types of light for therapeutic use in biological systems because NIR light can pass through blood and tissue to depths of several inches. However, very few organic chromophores absorb in this region, and even fewer are capable of converting the absorbed energy into a chemical or thermal response that can be used to trigger drug release. A few years ago, gold nanostructures (shells, particles, rods, and cages) emerged as useful agents for photothermal therapy after they were shown to have strong absorption in the NIR region (four to five times higher than conventional photo-absorbing dyes) as well as tunable optical resonances. The strong absorption enables effective laser therapy at relatively low laser energies, rendering such therapy methods minimally invasive.

Laser photothermal therapy of cancer with the use of gold nanoparticles immunotargeted to molecular markers has been reported as being effective to selectively kill cancer cells at lower laser powers than those needed to kill healthy cells. (X. Huang, et al., "Determination of the Minimum Temperature Required for Selective Photothermal Destruction of Cancer Cells with the Use of Immunotargeted Gold Nanoparticles", *Photochemistry and Photobiology*, 2006, 82:412-417.) Gold nanoparticles absorb light efficiently in the visible region due to coherent oscillations of metal conduction band electrons in strong resonance with visible frequencies of light, a phenomenon known as "surface plasmon resonance" or "SPR". Photoexcitation of metal nanostructures results in the formation of a heated electron gas that cools rapidly, e.g., within 1 ps, by exchanging energy with the nanoparticle lattice. The nanoparticle lattice, in turn, rapidly exchanges energy with the surrounding medium on the timescale of 100 ps, causing localized heating. This rapid energy conversion and dissipation can be achieved by using light radiation with a frequency that strongly overlaps the nanoparticle absorption band. Nanorods exhibit cylindrical symmetry, and simple changes in particle symmetry can significantly alter SPR characteristics. The NIR absorption maximum of metal nanostructures can be modulated by changing their size, shape and aggregation. GNRs have two plasmon absorption peaks, exhibiting transverse and longitudinal surface plasmon resonances that correspond to electron oscillations perpendicular and parallel to the rod length direction, respectively. The longitudinal surface plasmon wavelengths are tunable from the visible to infrared regions. The effectiveness of GNRs as photothermal therapeutic agents is strongly dependent on their scattering and absorption cross-sections—large absorption cross sections with small scattering losses allow for photothermal therapy with a minimal laser dosage. In addition, the longitudinal surface plasmon wavelengths of GNRs are preferably within the spectral range of 650-900 nm. Light irradiation in this region can penetrate more deeply into tissues and cause less photodamage than UV-visible irradiation. Therefore, the ability to tailor both scattering and absorption of GNRs with different longitudinal surface plasmon wavelengths is important for therapeutic applications.

BRIEF SUMMARY OF THE INVENTION

In an exemplary embodiment, the apparatus and method of the present invention combines near infrared (NIR) light exposure and a solution of gold nanorods (GNRs) that may be injected into the treatment target in order to selectively heat fat in the target area. The low power NIR light harmlessly penetrates the skin and overlying tissue to be absorbed only by the GNRs. The excited GNRs generate heat, melting the fat and tightening the skin. The liquefied melted fat can be removed with a syringe or fine cannula.

Only the regions into which the solution of gold nanorods has been injected are able to absorb the NIR wavelengths, which otherwise passes through the body virtually unnoticed. The amount of heating can be finely tuned by the nanorod dimensions, duration of exposure to the laser light and light intensity.

In one aspect of the invention, a system is provided for minimally-invasive fat removal from a target area, including a solution of photo-absorbing nanoparticles; means for injecting the solution into the target area; a near infrared light source for delivering a beam of light to the target area; at least one beam adjusting optical element for controlling focus and beam size within the target area; a system controller for providing control signals to the infrared light source, wherein the control signals comprise selection of an emission wavelength, an emission intensity and an exposure duration, and wherein the emission wavelength is adapted to excite the nanoparticles to melt fat within the target area; and means for extracting melted fat from the target area. In a preferred embodiment, the nanoparticles are biocompatible, and photoabsorption in the nanoparticles is mediated by surface plasmon resonance. The nanoparticles may be selected to absorb in the near infrared range (700-900 nm) and in the preferred embodiment are gold nanorods. The gold nanorods may have an aspect ratio in the range of 1:3-1:5, with an axial diameter of approximately 10 nm and a longitudinal diameter in the range of 9-50 nm. The gold nanorods may be suspended in water at a concentration of $3 \times 10^{11}$ GNR/mL. The near infrared light source may be a NIR laser having tunable power and/or wavelength, and further comprising beam adjusting optical means for control of beam size at the target area and may emit light within the wavelength range of 600 nm to 950 nm, more preferably in the range of 700 nm to 900 nm, and most preferably around 800 nm.

In another aspect of the invention, a photothermal method is provided for in vivo fat removal by melting the fat using the system that includes a solution of photo-absorbing nanoparticles; means for injecting the solution into the target area; a near infrared light source for delivering a beam of light to the target area; at least one beam adjusting optical element for controlling focus and beam size within the target area; a system controller for providing control signals to the infrared light source, wherein the control signals comprise selection of an emission wavelength, an emission intensity and an exposure duration, and wherein the emission wavelength is adapted to excite the nanoparticles to melt fat within the target area; and means for extracting melted fat from the target area.

In still another aspect of the invention, a method is provide for inducing skin tightening around regions from which adipose tissue has been removed using the system that includes a solution of photo-absorbing nanoparticles; means for injecting the solution into the target area; a near infrared light source for delivering a beam of light to the target area; at least one beam adjusting optical element for controlling focus and beam size within the target area; a system controller for providing control signals to the infrared light source, wherein the control signals comprise selection of an emission wavelength, an emission intensity and an exposure duration, and wherein the emission wavelength is adapted to excite the nanoparticles to melt fat within the target area; and means for extracting melted fat from the target area.

Another aspect of the invention is a photothermal agent for melting fat and skin tightening comprising photo-absorbing nanoparticles suspended in a solution, wherein the photo-absorbing nanoparticles are adapted to convert NIR light energy into fat-melting heat in a target area in which the nanoparticles have been injected. In a preferred embodiment, the nanoparticles are gold nanorods.

Yet another aspect of the invention is a kit for in vivo photothermal removal of fat in a target area irradiated by NIR light energy, the kit including photo-absorbing nanoparticles suspended in a solution, wherein the photo-absorbing nanoparticles are adapted to convert NIR light energy into heat having a temperature that melts fat; a first syringe adapted for injecting the nanoparticle solution into a target area; and a second syringe or cannula adapted for aspirating melted fat from the target area after exposure of the target area to NIR light energy for period of time sufficient to melt the fat.

The combination of gold nanorods and NIR light to thermalize adipose and skin has not heretofore been disclosed. This combination offers unparalleled spatial and temporal control that no existing technique offers. The result is fat melting with ease, and minimal postoperative pain by eliminating unnecessary damage to blood vessels and nerves. It is important to note here that the prior art techniques emulsify fat, breaking it down into small globules—they do not melt fat. This has direct implications on how the fat can be removed. As a result, the inventive technique is expeditious and minimally invasive, eliminating the need to use larger, traumatizing cannulas that are inserted through small incisions.

BRIEF DESCRIPTION OF THE DRAWINGS

FIG. 3A shows absorption in the visible range and FIG. 3B shows absorption with the visible range removed.

DETAILED DESCRIPTION

Disclosed herein are a method and system which combine gold nanorods, near infrared light and minor medical procedures to reduce and remove fatty tissue. By injecting a small volume of a solution of gold nanorods into the targeted area, the invention provides for the selective melting of fat and the tightening of skin upon illumination using a low power, biologically benign Near Infrared (NIR) laser.

Figure 1:
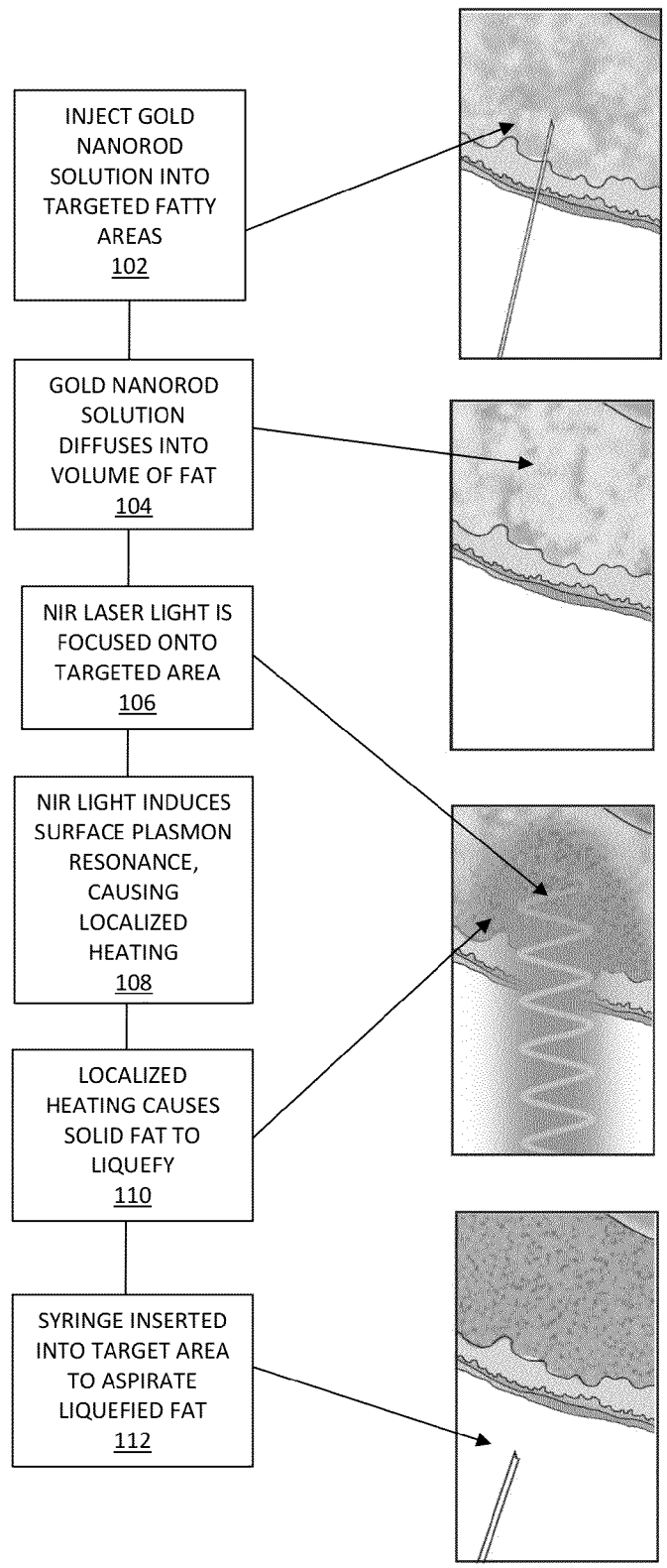
FIG. 1 illustrates an exemplary sequence of steps in a procedure for selective fat removal according to the present invention.

FIG. 1 illustrates the process flow for the inventive method, with each process step linked by an arrow to a diagrammatic image of the step as performed on a target area of a patient. The flexibility in the laser diameter, shape and intensity allows precise control over the target area, which may vary from very small, on the order of a few millimeters, to relatively large, e.g., several centimeters in diameter. In step 102, the physician administers a subcutaneous injection into the target area of a solution of gold nanorods (GNRs) suspended in a sterile, inert liquid, e.g., distilled water, using a fine syringe. In step 104, the GNR solution diffuses through the adipose tissue to be targeted. Immediately after injection, or as soon as practically possible, NIR laser light is focused onto the target area (step 106) for a period that may range from a few seconds to several minutes, depending on the area and volume of the targeted fat, and at least for a sufficient period of time to induce surface plasmon resonance within the GNRs. The laser light has a wavelength within the range of 600 nm to 950 nm, preferably within the range of 700 nm to 900 nm, and more preferably about 800 nm. In step 108, SPR is induced, producing localized heating which, in step 110, causes the solid fat to liquefy. Finally, in step 112, the physician inserts a syringe into the targeted area to aspirate the liquefied fat.

A similar procedure may be used to heat and thus stimulate the surrounding skin to minimize sagging after adipose tissue removal. In such a procedure, the GNR solution may be applied directly to the skin or injected intradermally prior to irradiation by the NIR laser light.

Figure 2:
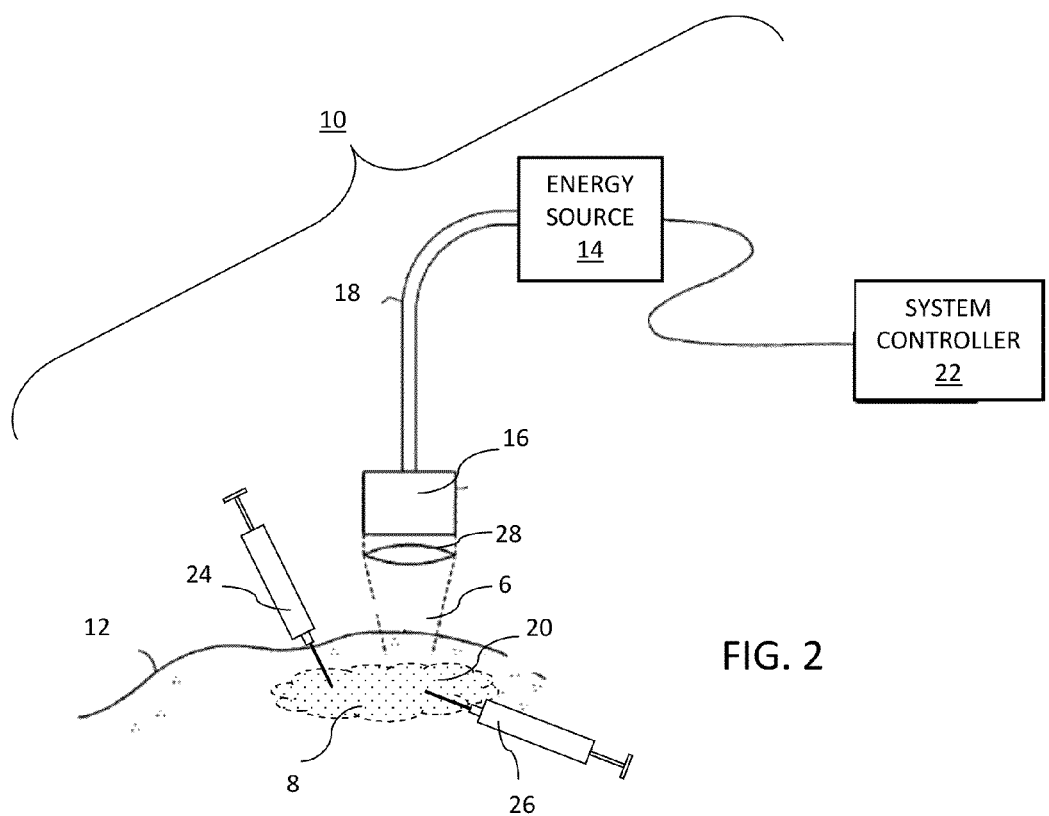
FIG. 2 is a diagrammatic view of a kit and apparatus for performing selective fat removal.

FIG. 2 is a representative schematic diagram of the components of the system 10 of the present invention. The GNRs 8 (in solution) are injected into the target tissue 20 using syringe 24. The GNRs are preferably suitable for in vivo use, for example, a polymer coating can be added for long circulation. The GNR's should be sterilized and certified endotoxin-free. The NIR laser energy 6 from the energy source 14 is directed into delivery device 16 via a delivery channel 18, which may be a fiber optic, articulated arm, or other appropriate optical waveguide. In preferred embodiments, the NIR laser is tunable to allow selection of a wavelength that is optimized for different size GNRs. The laser should preferably have adjustable power to modulate the degree of heating. Control system 22 provides a user interface for use by the physician, or assisting nurse or technician, to select the appropriate laser wavelength, intensity, duration and other parameters that may affect the treatment. At the distal end of delivery device 16 is an energy directing means 28 for directing the pulsed energy toward the surface tissue 12 overlying the target tissue (fat) 20. The directing means 28 may be one or more optical elements such as a lens or other focusing element, beam shaping optics, slits, apertures, gratings, an array of lenses and other optics or other focusing configuration, which focuses the beam within the targeted volume of fat containing the GNRs. In a preferred embodiment, the optical elements may include beam expanding lenses to allow adjustment of the beam spread to cover different size target areas. Following irradiation of the GNRs in the fatty tissue to liquefy the fat 20, the liquid is aspirated using syringe 26 that is inserted into the pocket of liquefied fat. The invention further includes a kit for performing selective fat removal in conjunction with an existing NIR laser unit. The kit includes the GNRs 8 in solution and syringes 24 and 26. The syringe for extracting the liquefied fat may be replaced by a fine cannula connected to a vacuum source that is capable of generating suction at the distal end of the cannula sufficient to draw the liquefied fat from the target area and into a collection vessel.

The inventive technique is possible because NIR light of low power is minimally absorbed by endogenous components in the body, such as skin, water, hemoglobin. Furthermore, low power near infrared light does not cause photodamage to tissue. NIR light is currently used for imaging using Indocyanine green (ICG), an FDA approved imaging agent able to absorb and emit in this region. While skin and adipose tissue do not absorb the NIR wavelengths, GNRs do, enabling fine tuning of the spatiotemporal parameters of heating.

Because the fat is actually liquefied, the inventive method for selective fat removal has the further advantage of being able to use needles or cannulas that are much smaller in diameter (on the order of 16 or 18 gauge) than those required for conventional liposuction, thus reducing patient discomfort, minimizing the risk of damage to surrounding tissue, reducing the risk of scarring and infection, and accelerating healing at the site of the procedure. Another major improvement over the prior art methods is the duration of treatment. The highly selective and rapid heating produced by the excited GNRs is capable of producing the desired results within minutes, in contrast with the multiple hours required by typical liposuction procedures.

The following examples demonstrate the principles used in the present invention.

EXAMPLE 1

Photothermal Melting of Butter

To demonstrate the selective photothermal melting of fat, we performed experiments on a ~2 mm layer of butter sandwiched between two slides separated by a silicone spacer small. Gold nanorods (GNRs) were procured from Nanopartz™ specifically "Ntracker™ for in vivo Therapeutics" gold nanorods coated in a proprietary dense layer of hydrophilic polymers, with 10 nm axial diameter and 42 nm length. According to information provided by Nanopartz, at this aspect ratio, the plasmon absorption peaks are at 817 nm and 512 nm. Laser heating was conducted on butter samples with and without GNRs using an unfocused (~2 mm diameter) 800 nm beam from a Ti-Sapphire (100 fs, 80 MHz) laser. The GNR-butter samples were prepared from a mixture of 10 µL of $3 \times 10^{12}$ GNR/mL with ~50 mg of butter. Melting was monitored by visual inspection.

The melting point of butter is 32-38° C. and its specific heat is ~5 joules/g° C. This means that with the ~2 mm diameter beam at 800 nm at 0.45 W power (14 W/cm$^2$), the illuminated butter sample should heat at a rate of approximately 2 degrees every second. The input heat and resulting heating rate is likely less in actuality because of absorption of the microscope slide glass.

Figure 3A:
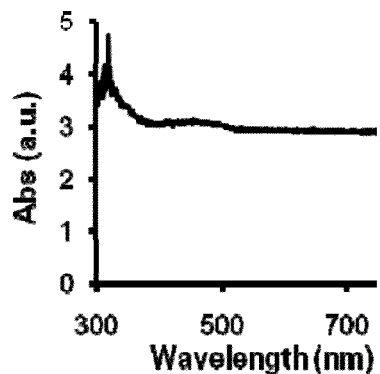
FIGS. 3A and 3B are plots of wavelength versus absorption, where
Figure 3B:
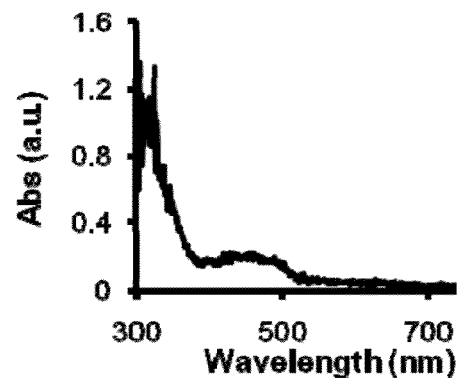

The butter sample used in these experiments shows no absorption in the region of the laser illumination wavelength, 800 nm, as shown in FIGS. 3A and 3B. The primary contribution to absorption is the fatty acids in the milk fat, which absorb in the visible range of the spectrum. The opacity of the sample limits the transmission of light through the butter so the optical density is high, as shown in the plot of FIG. 3A. If the contribution of the light scattering to the spectrum is removed, the absorption due to the butter can be better visualized, as shown in FIG. 3B.

Figure 4:
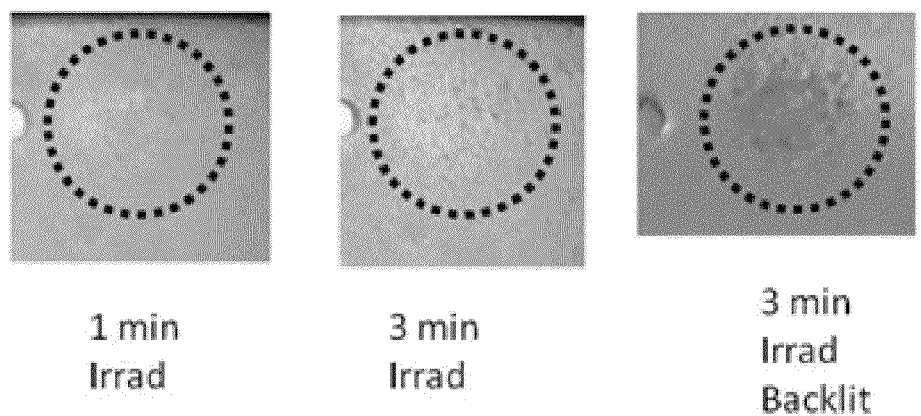
FIG. 4 shows three photographs demonstrating the absence of melting under different laser heating conditions.
Figure 5A:
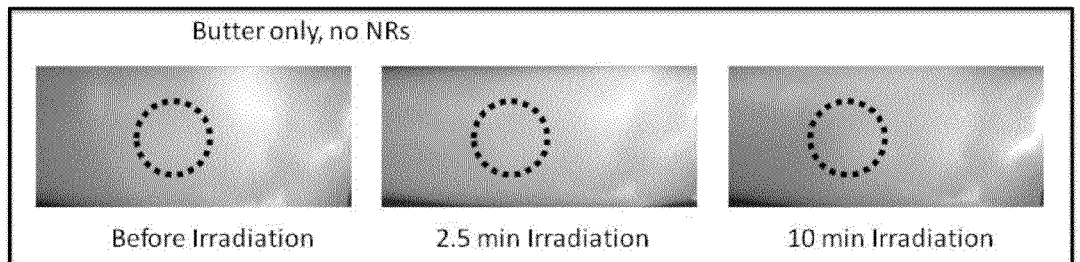
FIGS. 5A and 5B are photographs of butter samples before and after laser irradiation with and without gold nanorods, respectively.

Experiments on a plain butter sample showed that melting does not occur after 3 minutes, shown in the photos of FIG. 4, and up to 10 minutes, shown in FIG. 5A, of illumination with a 0.45 W laser beam.

Figure 5B:
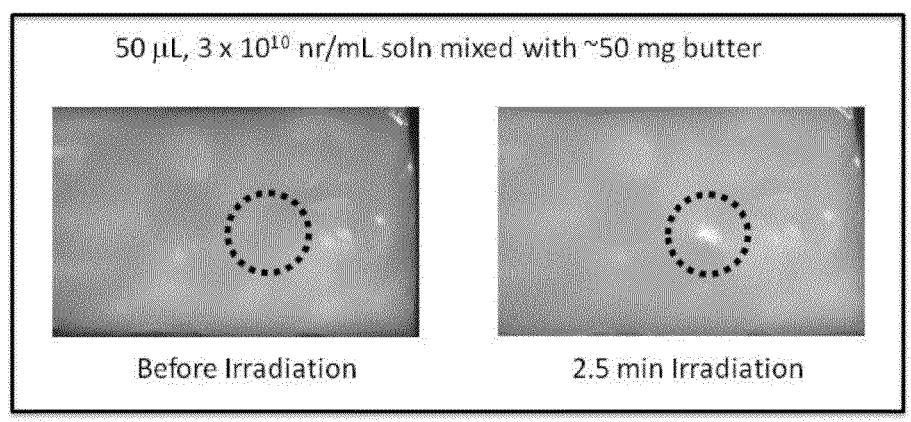

In the case of the GNR-butter sample under similar experimental conditions, melting of the butter was observed in the area irradiated by the NIR laser beam after 2.5 minutes of illumination. FIG. 5B shows the butter before and after irradiation.

Example 2

Photothermal Melting of Meat and Fat

Figure 6A:
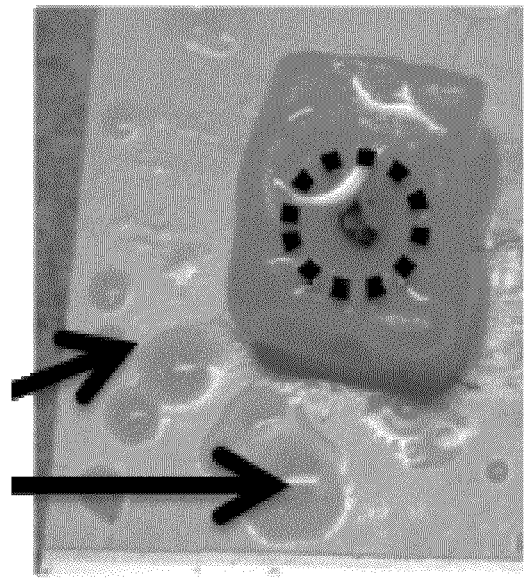
FIGS. 6A-6B are photographs of bacon fat samples with and without gold nanorods after exposure to NIR laser heating.
Figure 6B:
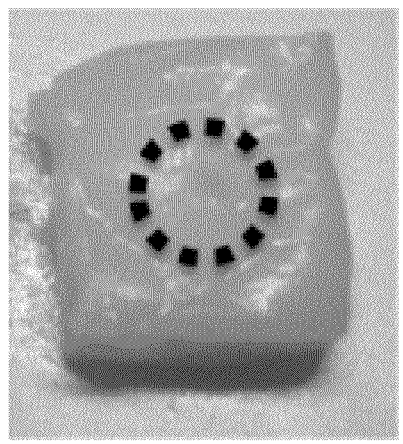
Figure 6C:
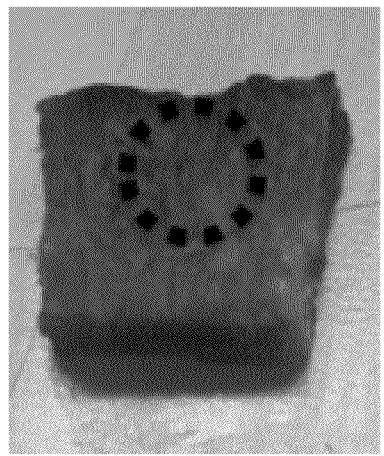
FIG. 6C is a photograph of bacon meat without gold nanorods after NIR laser irradiation.

Testing was also performed on bacon samples to compare the heating behavior in fat versus meat. We added 10 µL of $3\times10^{12}$ GNR/mL in water onto the fatty sections of the bacon and illuminated the treated sections with a ~2 mm diameter 800 nm beam at 2.5 W power. Melting of the GNR-injected fat was observed after 45 sec in the volume traversed by the laser beam where GNRs were present. Illumination was maintained for a total of 1.5 min to further melt the fat and determine whether charring can occur when high temperatures are attained. As shown in FIG. 6A, charring was observed. The melted fat (grease) became so hot that it splattered around the fat sample, indicated by the arrows in the figure. Control experiments on similarly irradiated non-GNR fat showed no melting (FIG. 6B). After irradiation, the fat had the same appearance as non-irradiated samples. The irradiated meat sections without GNRs were similarly unaffected (FIG. 6C). These results demonstrate the highly selective nature of the heating in the GNR-injected areas of fat versus untreated areas.

Experiments indicate that a solution of approximately $3\times10^{12}$ GNR/mL in water would be an effective injectable photothermal agent for melting adipose tissue upon irradiation with a NIR laser as a prelude to in-vivo fat removal. For the removal of 50 mL of fat, less than 10 mL of the GNR may be required. At the price of $500 per liter of $3\times10^{12}$ GNR/mL, the method provides an affordable alternative to conventional liposuction approaches.

The application of this technology has many secondary benefits in addition to the cosmetic effect of eliminating body fat. For example, illnesses such as diabetes mellitus are directly related to fat storage and obesity. Insulin resistance can be eliminated by reducing body fat content. This scientific fact has significant implications on chronic illnesses such as diabetic nephropathy, diabetic retinopathy and coronary heart disease. To date, existing techniques have not exhibited the ability to remove an effective amount of fatty tissue without causing severe damage to adjacent tissue. In addition, during existing procedures, patients are exposed to the potentially dangerous effects of lidocaine toxicity, which is included in current tumescent solutions.

The controlled thermal melting of fat protects all other vital structures, reducing post operative pain and, hence, reducing the amount of lidocaine needed in a tumescent solution and avoid life-threatening risks of lidocaine toxicity. The fact that no-to-minimal mechanical force is required to practice the inventive technique further eliminates the risk of penetrating deep tissues. Penetration of tissues such as bowels, livers and lungs has been reported in the literature with use of excessive force to achieve adequate liposuction.

REFERENCES

Incorporated Herein by Reference

1. R. Weissleder, A clearer vision for in vivo imaging, Nat. Biotechnol. 19 (2001) 316-317.
2. S. J. Oldenburg, J. B. Jackson, S. L. Westcott, N. J. Halas, Infrared extinction properties of gold nanoshells, Appl. Phys. Lett. 75 (1999) 2897-2899.
3. L. R. Hirsch, R. J. Stafford, J. A. Bankson, S. R. Sershen, B. Rivera, R. E. Price, J. D. Hazle, N. J. Halas, J. L. West, Nanoshell-mediated near-infrared thermal therapy of tumors under magnetic resonance guidance, Proc. Natl. Acad. Sci. U.S.A. 100 (2003) 13549-13554.
4. Y. N. Xia, P. D. Yang, Y. G. Sun, Y. Y. Wu, B. Mayers, B. Gates, Y. D. Yin, F. Kim, Y. Q. Yan, One-dimensional nanostructures: synthesis, characterization, and applications, Adv. Mater. 15 (2003) 353-389.
5. V. P. Zharov, V. Galitovsky, M. Viegas, Photothermal detection of local thermal effects during selective nanophotothermolysis, Appl. Phys. Lett. 83 (2003) 4897-4899.
6. J. Lee, A. O. Govorov, N. A. Kotov, Nanoparticle assemblies with molecular springs: a nanoscale thermometer, Angew. Chem. Int. Ed. 44 (2005) 7439-7442.
7. W. Huang, W. Qian, M. A. El-Sayed, Gold nanoparticles propulsion from surface fueled by absorption of femtosecond laser pulse at their surface plasmon resonance, J. Am. Chem. Soc. 128 (2006) 13330-13331.
8. H. Takahashi, T. Niidome, A. Nariai, Y. Niidome, S. Yamada, Gold nanorodsensitized cell death: microscopic observation of single living cells irradiated by pulsed near-infrared laser light in the presence of gold nanorods, Chem. Lett. 35 (2006) 500-501.
9. J. Y. Chen, D. L. Wang, J. F. Xi, L. Au, A. Siekkinen, A. Warsen, Z. Y. Li, H. Zhang, Y. N. Xia, X. D. Li, Immuno gold nanocages with tailored optical properties for targeted photothermal destruction of cancer cells, Nano Lett. 7 (2007) 1318-1322.
10. J. Chen, F. Saeki, B. J. Wiley, H. Cang, M. J. Cobb, Z. Y. Li, L. Au, H. Zhang, M. B. Kimmey, X. D. Li, Y. Xia, Gold nanocages: bioconjugation and their potential as optical imaging contrast agents, Nano Lett. 5 (2005) 473-477.
11. P. K. Jain, K. S. Lee, I. H. El-Sayed, M. A. El-Sayed, Calculated absorption and scattering properties of gold nanoparticles of different size, shape, and composition: applications in biological imaging and biomedicine, J. Phys. Chem. B 110 (2006) 7238-7248.
12. S. Link, M. A. El-Sayed, Shape and size dependence of radiative, non-radiative and photothermal properties of gold nanocrystals, Int. Rev. Phys. Chem. 19 (2000) 409-453.
13. B. G. Prevo, S. A. Esakoff, A. Mikhailovsky, J. A. Zasadzinski, Scalable routes to gold nanoshells with tunable sizes and response to near-infrared pulsed-laser irradiation, Small 4 (2008) 1183-1195.
14. G. Wu, A. Mikhailovsky, H. A. Khant, C. Fu, W. Chiu, J. A. Zasadzinski, Remotely triggered liposome release by near-infrared light absorption via hollow gold nanoshells, J. Am. Chem. Soc. 130 (2008) 8175-8177.
15. D. V. Volodkin, A. G. Skirtach, H. Moehwald, Near-IR remote drug release from assemblies of liposomes and nanoparticles, Angew. Chem. Int. Ed. 48 (2009) 1807-1809.

16. X. H. Huang, P. K. Jain, I. H. El-Sayed, M. A. El-Sayed, Plasmonic photothermal therapy (PPTT) using gold nanoparticles, Laser Med. Sci. 23 (2008) 217-228.
17. Lynch, D. J., Iverson, R. E., and the American Society of Plastic Surgeons Committee on Patient Safety. Practice advisory on liposuction. Plast. Reconstr. Surg. 113: 1478; discussion 1491; discussion 1494, 2004.
18. Beran, S. J., and Rohrich, R. J. Body contouring (overview). Select. Read. Plast. Surg. 8: 1, 1998.
19. Weniger, F. G., Calvert, J. W., and Newton, E. D. Liposuction of the legs and ankles: A review of the literature. Plast. Reconstr. Surg. 113: 1771, 2004.
20. Pitman, G. H. Liposuction and body contouring. In S. J. Aston (Ed.), Grabb and Smith's Plastic Surgery, 5th Ed. Philadelphia: Lippincott-Raven, 1997.
21. Fodor, P. B., and Watson, J. P. Wetting solutions in ultrasound-assisted lipoplasty. Clin. Plast. Surg. 26: 289, 1999.
22. Klein, J. A. Tumescent technique for local anesthesia improves safety in large-volume liposuction. Plast. Reconstr. Surg. 92: 1085, 1993.
23. Pitman, G. H., Aker, J. S., and Tripp, Z. D. Tumescent liposuction. Clin. Plast. Surg. 26: 289, 1999.
24. Rubinstein, E. F. An anesthesiologist's perspective of lipoplasty. Clin. Plast. Surg. 26: 423, 1999.
25. Brown, S. A., Lipschitz, A. H., Kenkel, J. M., et al. Pharmacokinetics and safety of epinephrine use in liposuction. Plast. Reconstr. Surg. 114: 756, 2004.
10. Friedberg, B. L. Liposuction "conscious sedation" monitored anesthesia care and level of consciousness monitoring (Letter). Aesthetic Plast. Surg. 29: 59, 2005.
26. Rohrich, R. J., Beran, S. J., and Fodor, P. B. The role of subcutaneous infiltration in suction-assisted lipoplasty: A review. Plast. Reconstr. Surg. 99: 514, 1997.
12. Commons, G. W., Halperin, B., and Chang, C. C. Large-volume liposuction: A review of 631 consecutive cases over 12 years. Plast. Reconstr. Surg. 108: 1753, 2001.
27. Horton, J. B., Reece, E. M., Broughton, G., Janis, J. E., Thornton, J. F., and Rohrich, R. J. Patient safety in the office-based setting. Plast. Reconstr. Surg. 117: 61e, 2006.
28. Keyes, G. R., Singer, R., Iverson, R. E., et al. Analysis of outpatient surgery center safety using an internet-based quality improvement and peer review program. Plast. Reconstr. Surg. 113: 1760, 2004.
29. Trott, S. A., Beran, S. J., Rohrich, R. J., Kenkel, J. M., Adams, W. P., Jr., and Klein K. W. Safety considerations and fluid resuscitation in liposuction: An analysis of 53 consecutive patients. Plast. Reconstr. Surg. 102: 2220, 1998.
30. Fodor, P. B. Power-assisted lipoplasty versus traditional suction-assisted lipoplasty: Comparative evaluation and analysis of output (Letter). Aesthetic Plast. Surg. 29: 127, 2005.
31. Gingrass, M. K. Lipoplasty complications and their prevention. Clin. Plast. Surg. 26: 341, 1999.
32. Kim, J., and Stevenson, T. R. Abdominoplasty, liposuction of the flanks, and obesity: Analyzing risk factors for seroma formation. Plast. Reconstr. Surg. 117: 773, 2006.
33. Rohrich, R. J., Broughton, G., Horton, B., Lipschitz, A. H., Kenkel, J. M., and Brown, S. A. The key to long-term success in liposuction: A guide for plastic surgeons and patients. Plast. Reconstr. Surg. 114: 1945, 2004.

The invention claimed is:

1. A method for selective fat removal in a target area, comprising:
applying a solution of photo-absorbing biocompatible nanoparticles to the target area, wherein the nanoparticles are dimensioned to have an aspect ratio in the range of 1:3 to 1:5;
delivering near infrared light to the target area and solution for an exposure duration to induce surface plasmon resonance, wherein the near infrared light has a combination of optical parameters selected from the group consisting of emission wavelength, emission intensity, beam focus and a beam size, the optical parameters and the exposure duration selected to excite the nanoparticles to melt and liquefy fat within the target area with minimal damage to tissue surrounding the target area; and
aspirating liquefied fat from the target area.
2. The method of claim 1, wherein the emission wavelength is within a range of 700-900 nm.
3. The method of claim 1, wherein the nanoparticles are gold nanorods.
4. The method of claim 3, wherein the gold nanorods have an axial diameter of approximately 10 nm and a longitudinal diameter in the range of 9-50 nm.
5. The method of claim 3, wherein the solution comprises gold nanorods suspended in water at a concentration of $3 \times 10^{11}$ GNR/mL.
6. The method of claim 1, wherein the near infrared light is delivered by a NIR laser having at least one of tunable power and tunable wavelength.
7. The method of claim 6, wherein the tunable power is within the range of 0.6 to 15 W.
8. The method of claim 1, wherein the beam size is within the range of 1 mm to 5 mm diameter.
9. The method of claim 1, wherein the exposure duration is within the range of 30-45 seconds.
10. The method of claim 1, wherein in the target area is located beneath a NIR-light transmissive surface.
11. The method of claim 10, wherein the NIR-light transmissive surface is skin and the step of applying the solution comprises subcutaneous injection.
12. The method of claim 11, wherein the method further comprises tightening skin adjacent the target area.
13. A method for subcutaneous fat removal and skin tightening in a person in need thereof, the method comprising:
subcutaneously injecting a suspension of photo-absorbing gold nanorods in solution into a target region of the person, the gold nanorods having an aspect ratio in the range of 1:3 to 1:5;
directing NIR light energy to the target area for an exposure duration, the NIR light energy having optical parameters adapted to pass through the person's skin and excite the gold nanorods in the target region to produce heat having a sufficient temperature to melt and liquefy fat within the target region with minimal damage to tissue surrounding the target region; and
extracting liquefied fat from the target region.
14. The method of claim 13, wherein the optical parameters comprise an emission wavelength within a range of 700-900 nm.
15. The method of claim 13, wherein the gold nanorods have an axial diameter of approximately 10 nm and a longitudinal diameter in the range of 9-50 nm.
16. The method of claim 13, wherein the gold nanorods are suspended in water at a concentration of $3 \times 10^{11}$ GNR/mL.
17. The method of claim 13, wherein the NIR light energy is delivered by a NIR laser having at least one of tunable power and tunable wavelength.

18. The method of claim 17, wherein the optical parameters comprise an NIR laser beam size within the range of 1 mm to 5 mm diameter.

19. The method of claim 17, wherein the optical parameters comprise a tunable power within the range of 0.6 to 15 W.

20. The method of claim 13, wherein the exposure duration is within the range of 30-45 seconds.

21. A method for fat removal and skin tightening in a subject in need thereof, the method comprising:
   subcutaneously injecting a suspension of gold nanorods having an aspect ratio in the range of 1:3 to 1:5 in solution into a target volume of fat in the subject;
   directing NIR laser light having a wavelength within a range of 700 to 900 nm to a skin area over the target volume for an exposure duration, the NIR laser light having optical parameters adapted to excite the gold nanorods within the target volume to produce heat having a temperature to melt and liquefy fat within the target volume with minimal damage to tissue surrounding the target volume; and
   inserting a cannula into and extracting liquefied fat from the target volume.

22. The method of claim 21, wherein the gold nanorods have an axial diameter of approximately 10 nm and a longitudinal diameter in the range of 9-50 nm.

23. The method of claim 21, wherein the gold nanorods are suspended in water at a concentration of $3 \times 10^{11}$ GNR/mL.

24. The method of claim 21, wherein the NIR laser light has at least one of tunable power and tunable wavelength.

25. The method of claim 24, wherein the NIR laser light has tunable power within a range of 0.6 to 15 W.

26. The method of claim 21, wherein the NIR laser light has a beam size within the range of 1 mm to 5 mm diameter.

27. The method of claim 21, wherein the exposure duration is within the range of 30-45 seconds.

28. A method for fat removal and skin tightening in a person in need thereof, the method comprising:
   subcutaneously injecting a suspension of gold nanorods having an axial diameter of approximately 10 nm and a longitudinal diameter in the range of 9-50 nm in solution into a target volume of fat in the person;
   directing NIR laser light having a wavelength within a range of 700 to 900 nm and a power within the range of 0.6 to 15 W onto a skin area over the target volume for an exposure duration, the NIR light energy having optical parameters adapted to excite the gold nanorods within the target volume to produce heat having a temperature to melt and liquefy fat within the target volume with minimal damage to tissue surrounding the target volume; and
   inserting a cannula into and extracting liquefied fat from the target volume.

* * * * *